United States Patent
Lopatin et al.

(10) Patent No.: US 8,220,313 B2
(45) Date of Patent: Jul. 17, 2012

(54) APPARATUS FOR ASCERTAINING AND/OR MONITORING A PROCESS VARIABLE OF A MEDUIM

(75) Inventors: Sergej Lopatin, Lörrach (DE); Alexander Müller, Sasbach-Jechtingen (DE); Sascha D'Angelico, Rümmingen (DE); Martin Urban, Zell i. W. (DE); Stanislaw Herwik, Rheinfelden (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 445 days.

(21) Appl. No.: 12/309,474

(22) PCT Filed: Jun. 14, 2007

(86) PCT No.: PCT/EP2007/055907
§ 371 (c)(1),
(2), (4) Date: Nov. 17, 2009

(87) PCT Pub. No.: WO2008/009522
PCT Pub. Date: Jan. 24, 2008

(65) Prior Publication Data
US 2010/0083752 A1    Apr. 8, 2010

(30) Foreign Application Priority Data

Jul. 19, 2006 (DE) .................. 10 2006 033 819

(51) Int. Cl.
*G01N 9/00* (2006.01)
(52) U.S. Cl. ..................................................... 73/32 R
(58) Field of Classification Search .................. 73/32 R, 73/32 A, 1.02, 453
See application file for complete search history.

(56) References Cited

U.S. PATENT DOCUMENTS

| | | | | |
|---|---|---|---|---|
| 3,170,094 A * | 2/1965 | Roth | ............................. | 361/178 |
| 4,383,443 A * | 5/1983 | Langdon | ..................... | 73/290 V |
| 4,594,584 A * | 6/1986 | Pfeiffer et al. | ................ | 340/620 |
| 4,601,200 A * | 7/1986 | Stoffelen | .................... | 73/290 V |
| 5,043,912 A * | 8/1991 | Reus | ............................. | 702/54 |
| 6,044,694 A * | 4/2000 | Anderson et al. | ............ | 73/54.41 |
| 6,148,665 A * | 11/2000 | Getman et al. | .............. | 73/290 V |
| 6,236,322 B1 * | 5/2001 | Lopatin et al. | ................. | 340/612 |
| 6,389,891 B1 * | 5/2002 | D'Angelico et al. | ........ | 73/290 V |
| 6,718,832 B1 * | 4/2004 | Hay et al. | ........................ | 73/790 |
| 6,860,136 B1 * | 3/2005 | Hay et al. | ........................ | 73/1.01 |
| 7,068,050 B2 * | 6/2006 | Steele et al. | .................. | 324/640 |

(Continued)

FOREIGN PATENT DOCUMENTS

DE        28 31 963        2/1979

(Continued)

*Primary Examiner* — Hezron E Williams
*Assistant Examiner* — Samir M Shah
(74) *Attorney, Agent, or Firm* — Bacon & Thomas, PLLC

(57) ABSTRACT

An apparatus for ascertaining and/or monitoring a process variable, especially density of a medium. The apparatus includes: an exciting/receiving unit, which excites a mechanically oscillatable unit to execute mechanical oscillations and which receives the mechanical oscillations; an electronics unit, which applies to the exciting/receiving unit an electrical, exciter signal, and which obtains from the exciting/receiving unit an electrical, received signal. The electronics unit produces the exciter signal in such a manner, that, between the received signal and the exciter signal, a phase difference equal to a desired value of phase difference results, at which effects of changes of viscosity on mechanical oscillations of the mechanically oscillatable unit are negligible, and that the desired value of phase difference is predetermined as a function of the ratio of impedance of the exciting/receiving unit to the input impedance of the electronics unit.

7 Claims, 1 Drawing Sheet

U.S. PATENT DOCUMENTS

| | | | | |
|---|---|---|---|---|
| 7,220,229 B2 * | 5/2007 | Lee et al. | .................. | 600/438 |
| 7,272,525 B2 * | 9/2007 | Bennett et al. | ............... | 702/100 |
| 7,409,874 B2 * | 8/2008 | Walsh et al. | ............... | 73/861.42 |
| 7,513,151 B2 * | 4/2009 | D'Angelico et al. | ....... | 73/290 R |
| 7,581,446 B2 * | 9/2009 | Troxler | ........................ | 73/623 |
| 7,681,445 B2 * | 3/2010 | Pfeiffer | ..................... | 73/290 V |
| 7,874,199 B2 * | 1/2011 | Chaudoreille et al. | ........ | 73/32 A |
| 8,011,248 B2 * | 9/2011 | Troxler | ........................ | 73/588 |
| 2004/0078164 A1 | 4/2004 | Lopatin | | |
| 2011/0023626 A1 * | 2/2011 | Weinstein | ............... | 73/861.357 |

FOREIGN PATENT DOCUMENTS

| | | |
|---|---|---|
| DE | 100 57 974 A1 | 5/2002 |
| EP | 0 985 916 | 3/2000 |

* cited by examiner

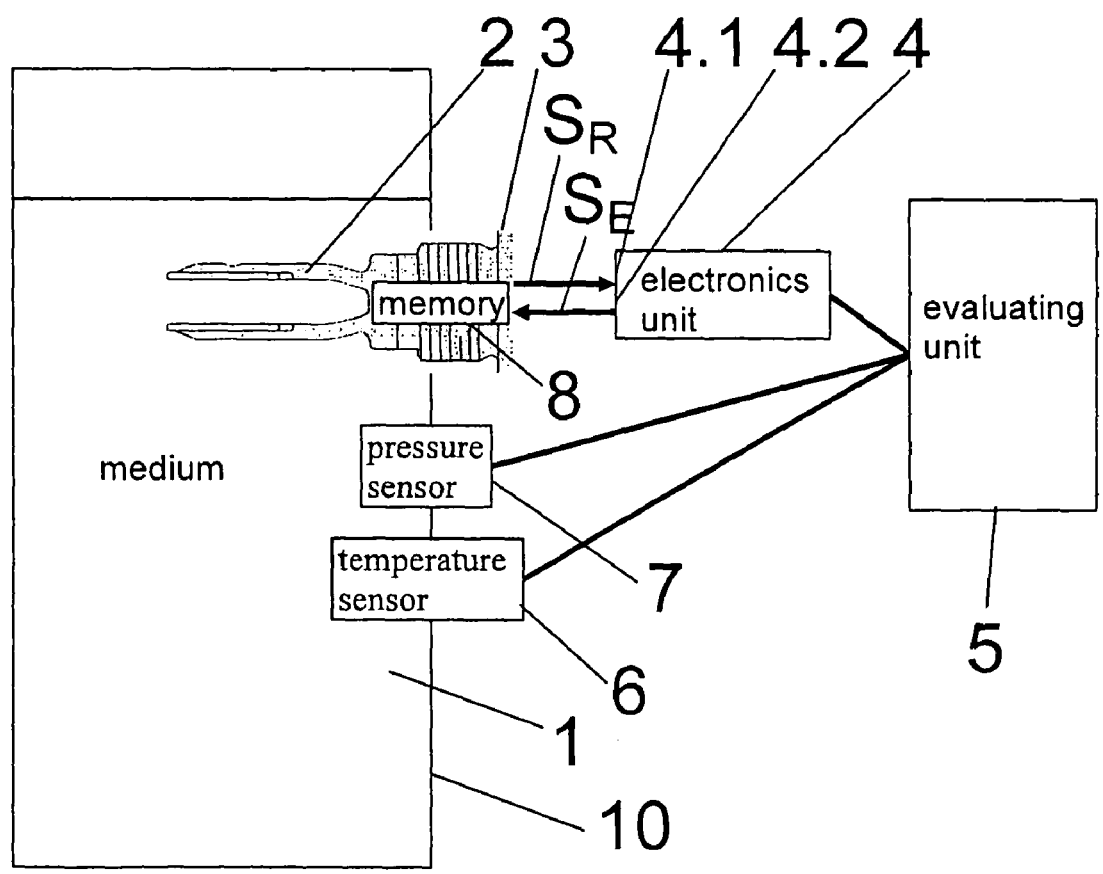

APPARATUS FOR ASCERTAINING AND/OR MONITORING A PROCESS VARIABLE OF A MEDUIM

TECHNICAL FIELD

The invention relates to an apparatus for ascertaining and/or monitoring at least one process variable, especially the density ρ of a medium. The apparatus includes: At least one mechanically oscillatory unit; at least one exciting/receiving unit, which excites the mechanically oscillatory unit, such that it executes mechanical oscillations, and which receives mechanical oscillations of the mechanically oscillatory unit; and at least one electronics unit, which supplies the exciting/receiving unit with an electrical exciter signal $S_E$, and which receives from the exciting/receiving unit an electrical, received signal $S_R$. The medium is, for instance, a liquid. The medium is located, for example, in a container, or it is flowing through a pipe, or tube. In an embodiment of the invention, the process variable is the density of the medium.

BACKGROUND DISCUSSION

In the state of the art, measuring devices are known, which include so-called oscillatory forks. These oscillatory forks are caused to oscillate, and the oscillations, which depend on whether there is contact with the medium and then on characteristics of the medium, are received and evaluated. The oscillations, i.e. their variables, such as frequency or amplitude, depend on fill level, i.e. the degree of covering of the oscillatory fork by the medium, as well as also on density or viscosity of the medium. The dual dependence of the oscillations on density and viscosity of the medium makes the monitoring of density difficult.

Offenlegungsschrift DE 100 57 974 A1 describes such an oscillatory fork and concerns, especially, suppression of the dependence of the oscillations on the viscosity of the medium. The effects of viscosity can be reduced, according to this Offenlegungsschrift, by having a phase other than 90° between exciter signal and received signal. For instance, in the case of liquid media, a desired phase is 70°. Such a phase largely eliminates the effect of viscosity.

In order to find a phase difference, at which viscosity changes have no effects on the frequency of the oscillations, for example, curves of different media are recorded showing phase difference between transmitted and received signals as a function of frequency of the transmitted signal. The intersection of the curves yields the sought phase difference. This is described, for example, in EP 0 985 916 A1 of the present assignee.

SUMMARY OF THE INVENTION

An object of the invention is to provide a measuring device for reproducibly measuring a process variable, especially density.

The object is achieved according to the invention by embodying the electronics unit in such a manner that: It produces the exciter signal ($S_E$) in such a manner that, between the received signal ($S_R$) and the exciter signal ($S_E$), a phase difference ($\Delta\phi$) results, which is essentially equal to a predeterminable desired-value of phase-difference ($\Delta\phi_{des}$); the desired-value of phase-difference ($\Delta\phi_{des}$) is predetermined in such a manner, that, at the desired-value of phase-difference ($\Delta\phi_{des}$), effects of changes of viscosity of the medium on the mechanical oscillations of the mechanically oscillatory unit are essentially negligible; and the desired-value of phase-difference ($\Delta\phi_{des}$) is predetermined at least as a function of the ratio of the impedance of the exciting/receiving unit to the input impedance of the electronics unit, wherein the input impedance of the electronics unit is with reference to that input, via which the electronics unit receives the received signal ($S_R$).

The exciting/receiving unit is, in an embodiment, a piezoelectric element, which converts the exciter signal ($S_E$), which is an electrical, alternating voltage, into mechanical oscillations. These oscillations are transmitted, for example via a membrane, or diaphragm, to the mechanically oscillatable unit, thus e.g. to a so-called oscillatory fork having two fork tines. The mechanical oscillations, which are influenced by contact with the medium, or, at a more detailed level, by properties of the medium, are converted by the exciting/receiving unit, in turn, into an electrical, received signal ($S_R$), which includes at least the frequency ($F_0$) of the mechanical oscillations of the mechanically oscillatable unit.

For measuring density (ρ), it is especially important, that dependence on viscosity change be eliminated. Viscosity represents a damping of the oscillations. From theory, it is known, that an independence of damping is present, when, between the exciter signal and the received signal, a phase of +90° is present. As is, however, to be understood, for example, from Offenlegungsschrift DE 100 57 974 A1, this effect can arise in real systems at values different from 90°. The invention is based, now, on the recognition, that the phase for viscosity independence depends at least on the ratio between the impedance of the exciting/receiving unit and the input impedance of the electronics unit. Consequently, according to the invention, with reference to the particular dimensioning of the measuring device, the impedance of the exciting/receiving unit and the input impedance of the electronics unit (this depends on the type of electronics unit) are measured, or the phase angle resulting from the construction of the measuring apparatus is taken into consideration, and the corresponding phase angle is set, in order to achieve independence of viscosity changes. In an embodiment, which relates to a certain arrangement of the measuring device, the phase, which the received signal displays with respect to the exciter signal, amounts to +46°. If the input impedance is a high number of ohms, i.e. it is at least an order of magnitude, or a factor of 10, greater than the impedance of the exciting/receiving unit, then the phase for viscosity independence is +42°. High input impedance is present, for example, in the case of voltage amplifiers. If the input impedance is very small, i.e. at least an order of magnitude smaller than the impedance of the exciting/receiving unit, then the phase-difference amounts to −48°. A small input impedance is present, for example, in the case of charge amplifiers. The phase of the received signal relative to the exciter signal amounts, thus, depending on construction of the electronics unit, to +46°, +42° or −48°. The absolute value of the phase thus lies, preferably, in the range between 40° and 50°. This is, thus, a marked deviation from the theoretical value of 90°.

In order that these phase values can be maintained, the electronics unit must produce the exciter signal in such a manner that it results, in sum, at all phases of value 0° or n*360° (n=1, 2, 3. . . ), since, on the whole, an oscillatory circuit is involved. I.e., the desired-value of phase difference ($\Delta\phi_{des}$) amounts, depending on the ratio, input impedance to impedance of the exciting/receiving unit, to −46°, −42° or +48°. For evaluating the received signal for ascertaining density of the medium, advantageously, at least one evaluating unit is provided, which ascertains from the frequency of the received signal ($S_R$) at least the density (ρ) of the medium.

The evaluating unit is, in such case, a component of the measuring device, or it is an external unit.

An embodiment includes that the desired value of phase difference ($\Delta\phi_{des}$) is predetermined at least as a function of the ratio of the impedance of the exciting/receiving unit to the input impedance of the electronics unit and as a function of the output impedance of the electronics unit, with the output impedance being with reference to that output, via which the electronics unit outputs the exciter signal ($S_E$). In this embodiment, thus, also a further dependence on the output impedance of the electronics unit is taken into consideration.

An embodiment provides, that the desired value of phase difference ($\Delta\phi_{des}$) is different from 90°. Especially, the absolute value of the desired value of phase difference ($\Delta\phi_{des}$) lies between 40° and 50°. The desired value of phase difference ($\Delta\phi_{des}$) is, in such case, so sized, that it and the phase value of the sensor, at which viscosity independence is present, together yield the value n*360° (n=0, 1, 2...). Thus, if, for example, this phase value between exciter signal and received signal is +46°, then the desired value of phase difference ($\Delta\phi_{des}$) is −46°.

An embodiment includes, that, in the case, where the input impedance of the electronics unit is greater, especially at least an order of magnitude greater, than the impedance of the exciter/receiver unit, the desired value of phase difference ($\Delta\phi_{des}$) amounts to −42°. This holds especially in the case of a sensor unit having a bimorph drive and fork tines with no coating.

An embodiment provides, that, in the case, in which the input impedance of the electronics unit is smaller, especially at least an order of magnitude smaller, than the impedance of the exciter/receiver unit, the desired value of the phase difference ($\Delta\phi_{des}$) amounts to +48°. Especially, an embodiment provides, that the desired value of phase difference ($\Delta\phi_{des}$) is −46°, so that the phase value of the received signal ($S_R$) relative to the exciter signal ($S_E$) amounts to +46°.

An embodiment includes, that the electronics unit is embodied in such a manner, that the electronics unit produces the exciter signal ($S_E$) in such a manner, that the exciter signal ($S_E$) is essentially a sinusoidal signal. In general, a rectangular signal is used as excitation signal for the sake of simplicity. If the amplification of the entire oscillatory system—i.e. the arrangement composed of the mechanically oscillatable unit and the electronics unit—has a value of one in the case of steady state, i.e. when attenuation, amplification and amplitude no longer change, because, for example, the fill level of the medium, with which the oscillatable unit interacts, no longer changes, then a sinusoid results. In most measuring devices, an amplification greater than one is used, so that a rectangular signal results. However, in this embodiment, a value of one is used for the density measurement. An advantage of the sinusoidal excitement is exactly that then no harmonics are excited, and the oscillatory energy is applied for only one mode.

An embodiment provides, that the evaluating unit is embodied in such a manner that the evaluating unit ascertains density ($\rho$) of the medium essentially according to the following formula:

$$\rho = \frac{1}{K} * \left[ \left( \frac{F_{0,Vac} + C*T}{F_{0,Med}} \right)^2 * (1 + D*P) - 1 \right],$$

wherein K is a coefficient for the density sensitivity of the mechanically oscillatable unit, $F_{0,Vac}$ is the frequency of the mechanical oscillations of the mechanically oscillatable unit in vacuum, C is a coefficient for the temperature sensitivity of the mechanically oscillatable unit, T is a temperature value for the medium, $F_{0,Med}$ is the frequency ($F_0$) of the mechanical oscillations of the mechanically oscillatable unit in the medium, D is a coefficient for the pressure sensitivity of the mechanically oscillatable unit, and P is a pressure value for the medium.

For the accurate measurement of the density, the dependence on pressure and temperature must be taken into consideration, or the corresponding values must be measured. If these variables are constant, or if their effects are negligible in the application, then the formula can also be correspondingly simplified:

$$\rho \approx \frac{1}{K'} * \left[ \left( \frac{F_{0,Vac}}{F_{0,Med}} \right)^2 - 1 \right],$$

Such a simplification is, above all, possible when essentially only a change of density is to be detected.

Density can thus be measured, or monitored, via the following steps:

First, a calibration of the measuring device is done:
dependence of the mechanical oscillations of the mechanically oscillatable unit on the temperature T of the medium is ascertained, and therefrom, a coefficient C is ascertained for the temperature sensitivity of the mechanically oscillatable unit;

dependence of the mechanical oscillations of the mechanically oscillatable unit on pressure P of the medium is ascertained, and therefrom, a coefficient D is ascertained for the pressure sensitivity of the mechanically oscillatable unit;

dependence of the mechanical oscillations of the mechanically oscillatable unit on density $\rho$ of the medium is ascertained and therefrom, a coefficient (K) for the density sensitivity of the mechanically oscillatable unit is ascertained;

frequency $F_{0,Vac}$ of the mechanical oscillations of the mechanically oscillatable unit in vacuum is ascertained; and a desired value of phase difference ($\Delta\phi_{des}$) between the exciter signal ($S_E$) and the received signal ($S_R$) is ascertained, at which effects of changes of viscosity on the mechanical oscillations of the mechanically oscillatable unit are essentially negligible.

Following this calibration, the ascertained values are suitably stored and the actual measurements are performed:

temperature T of the medium is ascertained, or a value for the temperature T of the medium is selectably set, i.e., for example, even disregarded;

pressure P of the medium is ascertained, or a value for the pressure P of the medium is selectably set, in that, for example, also pressure is disregarded;

the mechanically oscillatable unit is excited to execute mechanical oscillations;

the mechanical oscillations of the mechanically oscillatable unit are received and converted into a received signal $S_R$;

from the received signal $S_R$, the frequency $F_{0,Med}$ of the mechanical oscillations of the mechanically oscillatable unit in the medium is ascertained; and density $\rho$ of the medium is ascertained with the above-determined constants and values via the following formula:

$$\rho = \frac{1}{K} * \left[ \left( \frac{F_{0,Vac} + C*T}{F_{0,Med}} \right)^2 * (1 + D*P) - 1 \right]$$

Alternatively, the abbreviated formula is applied and essentially a change of density is displayed. The described manner of proceeding is, however, only an example, and can easily be adapted to other conditions.

The desired value of phase difference is, in such case, ascertained in an embodiment with steps as follows:

For at least two media with different viscosities, the dependence between frequency ($F_{0,Med}$) of the mechanical oscillations of the mechanically oscillatable unit is ascertained in each medium and the phase difference ($\Delta\phi$) between the exciter signal ($S_E$) and the received signal ($S_R$) is ascertained; and the phase range is ascertained, within which the phase differences ($\Delta\phi$) of the at least two media are essentially equal. If the media also have different densities, then the pertinent embodiment is to be followed. In a further embodiment, phase difference is ascertained as a function of a variable load resistance on the exciting/receiving unit, i.e. as a function of different input impedances of the electronics unit; i.e., in this way, the effect of the input impedance on the phase value to be determined can be ascertained.

In an embodiment, the method for ascertaining the phase range is expanded in the respect that the densities ρ of the at least two media are ascertained, and that, in the case, in which the density values of the at least two media differ, the effects of the density ρ on the frequency $F_{0,Med}$ of the oscillations are ascertained and taken into consideration. In the simplest case, the effect of density on the measuring is, in each case, calculated. This embodiment thus relates, especially, to the case in which the densities of the two measured media are different, so that the effects of density on the oscillations and, especially, on oscillation frequency are calculated, in order to obtain the frequency change, which results just from the viscosity change.

An embodiment of the apparatus of the invention includes, that at least one temperature sensor for ascertaining temperature (T) of the medium is provided, and/or that at least one temperature sensor for ascertaining pressure (P) of the medium is provided. These sensors permit a more accurate measuring of density, since then the effects of density and temperature can be taken into consideration.

BRIEF DESCRIPTION OF THE DRAWING

The invention will now be explained in greater detail on the basis of the appended drawing, the sole FIGURE of which shows as follows:

FIG. 1 a schematic representation of a measuring apparatus of the invention.

DETAILED DISCUSSION

FIG. 1 shows a medium 1 in a container 10. Mounted on the container 10 is the mechanically oscillatable unit 2 of a measuring device of the invention. In this case, such is a so-called oscillatory fork, i.e. two fork tines are attached to a membrane, or diaphragm. Behind the membrane, and mechanically coupled therewith, is the exciting/receiving unit 3, which, in the illustrated case, is a piezoelectric element. Piezoelectric element 3 is applied as a transducer between the mechanical oscillations and the electrical signals. Electronics unit 4 applies to the exciting/receiving unit 3 an electrical, exciter signal $S_E$. This electrical, alternating voltage is converted into mechanical oscillations, which cause the oscillatory fork 2 to oscillate. These oscillations of the mechanically oscillatable unit 2 depend, in such case, on the degree of covering of the fork by the medium 1, but also on properties of the medium 1 itself. Thus, the oscillations also depend on the density and the viscosity of the medium 1. Via this dependence, it is possible, conversely, to measure such variables, by suitably evaluating the received signal $S_R$ of the exciting/receiving unit 3. The measuring device is here so embodied, that, especially, the density of the medium 1 is ascertained and/or monitored. The fill level can, however, among others, also continue to be measured and/or monitored. It is also to be noted, that the invention described here is not limited to the application based on oscillatory forks, or single rods, but, can, instead, for example, also be applied to Coriolis flow measuring devices. For density measurement, it is, however, necessary, that, among other things, the dependence of the oscillations on viscosity be eliminated. This is accomplished by giving the received signal $S_R$ a special phase, at which changes of viscosity have no, or only negligible, effects on the oscillation frequency. In order that this phase of the received signal $S_R$ be maintained and in order that the resonance condition be met, that the sum of all phases in the oscillatory circuit equals n*360° with n=0, 1, 2, 3..., the electronics unit 4 is embodied in such a manner, that it correspondingly produces the exciter signal $S_E$. In such case, it has been found that this phase value depends at least on the ratio of the impedance of the driving/receiving unit 3 and the input impedance 4.1 of the electronics unit 4. Thus, the value is also dependent on the structure of the electronics unit 4, i.e., especially on its amplifier type. The theoretical value for the phase is 90°. It is found, however, that the phase in the case of a very high-ohm input 4.1 equals 42°, while, in the case of a low-ohm input 4.1, it equals −48°. Correspondingly, the desired values of phase difference $\Delta\phi_{des}$ are −42° and +48°, respectively. These particular values relate, however, also to the further development of the measuring device. An explanative model for these values is one wherein the electronics unit 4, or its input impedance, functions, in connection with the capacitive characteristic of the driving/receiving unit 3 (especially in the case where it is a piezoelectric element) as a high-pass. The phase value, or the desired value of phase difference $\Delta\phi_{des}$, or a value for the exciting/receiving unit 3, from which, in connection with the type of electronics unit 4, the desired value of phase difference $\Delta\phi_{des}$ results, is preferably stored in a memory unit 8, so that the electronics unit 4, or a microprocessor located therein, can access such.

In order to improve the measurements and to increase the performance of the measuring device, the oscillatory the circuit composed of the mechanically oscillatable unit 2, exciting/receiving unit 3 and electronics unit 4, is embodied in such a manner that the total amplification equals one. I.e., The attenuation of the oscillations by the medium 1 and the amplification of the electronics unit 4 must exactly mutually cancel one another. Therefore, it is also necessary that the amplification factor of the electronics unit 4 be adjustable and changeable. Furthermore, it is advantageous to have the exciter signal $S_E$ be a sinusoidal signal and not a rectangular signal as usual in the case of such oscillatory systems. Essentially, a fundamental wave-excitation takes place.

Additionally, effects of pressure and temperature affect the oscillations. If these two variables are constant or if their variations are only slight, then their effects on the density measurement can be neglected. If, however, a measurement is required, which is as accurate as possible, then temperature T and pressure P are measured by the sensors 6, 7, respectively. The evaluating unit 5, which is, here, an independent unit, then calculates the density from the mechanical oscillations, i.e. especially from the frequency and the two measured variables, temperature and pressure.

LIST OF REFERENCE CHARACTERS 1 medium
2 mechanically oscillatable unit
3 exciting/receiving unit 4 electronics unit
4.1 input of the electronics unit
4.2 output of the electronics unit
5 evaluating unit
6 temperature sensor
7 pressure sensor
8 memory unit
10 container

The invention claimed is:

1. An apparatus for determining or monitoring at least one process variable, of a medium, comprising:
  at least one mechanically oscillatable unit;
  at least one exciting/receiving unit, which excites said at least one mechanically oscillatable unit to execute mechanical oscillations and which receives the mechanical oscillations of said at least one mechanically oscillatable unit;
  an evaluating unit embodied in such a manner that it ascertains density of the medium essentially according to the following formula:

$$\rho = \frac{1}{K} * \left[ \left( \frac{F_{0,Vac} + C*T}{F_{0,Med}} \right)^2 * (1 + D*P) - 1 \right],$$

wherein:
  K is a coefficient for pressure sensitivity of said at least one mechanically oscillatable unit;
  $F_{0,Vac}$ is frequency of the mechanical oscillations of said at least one mechanically oscillatable unit in vacuum;
  C is a coefficient for temperature sensitivity of said at least one mechanically oscillatable unit;
  T is a temperature value for the medium;
  $F_{0,Med}$ is frequency ($F_0$) of the mechanical oscillations of said at least one mechanically oscillatable unit in the medium;
  D is a coefficient for pressure sensitivity of said at least one mechanically oscillatable unit; and
  P is a pressure value for the medium
  at least one electronics unit, which applies an electrical, exciter signal to said at least one exciting/receiving unit, and which obtains from said at least one exciting/receiving unit an electrical, received signal, wherein:
  said at least one electronics unit is embodied in such a manner that it produces the exciter signal in such a manner, that, between the received signal and the exciter signal, a phase difference results, which is essentially equal to a predeterminable, desired value of phase difference;
  the desired value of this phase difference is predetermined in such a manner the, at the desired value of the phase difference, effects of changes of viscosity of the medium on mechanical oscillations of said at least one mechanically oscillatable unit are essentially negligible;
  the desired value of phase difference is predetermined at least as a function of ratio of impedance of said at least one exciting/receiving unit to input impedance of said at least one electronics unit; and
  the input impedance is with respect to that input, via which said at least one electronics unit receives the received signal.

2. The apparatus as claimed in claim 1, wherein:
  the desired value of phase difference is predetermined at least as a function of the ratio of impedance of said at least one exciting/receiving unit to the input impedance of said electronics unit and as a function of output impedance of said at least one electronics unit; and
  the output impedance is with respect to that output, via which said at least one electronics unit outputs the exciter signal.

3. The apparatus as claimed in claim 1, wherein:
  the desired value of phase difference differs from 90°.

4. Apparatus as claimed in claim 3, wherein:
  for a case in which the input impedance of said at least one electronics unit is greater, especially an order of magnitude greater, than the impedance of said at least one exciting/receiving unit, the desired value of phase difference amounts to −42°.

5. The apparatus as claimed in claim 3, wherein:
  for a case in which the input impedance of said at least one electronics unit is smaller, especially an order of magnitude smaller, than the impedance of said at least one exciting/receiving unit, the desired value of phase difference amounts to +48°.

6. Apparatus as claimed in claim 1, wherein:
  said at least one electronics unit is embodied in such a manner that it produces the exciter signal in such a manner that the exciter signal is essentially a sinusoidal signal.

7. The apparatus as claimed in claim 1, further comprising:
  at least one pressure sensor for ascertaining pressure of the medium.

* * * * *